United States Patent [19]

Bernard

[11] Patent Number: 4,619,902
[45] Date of Patent: Oct. 28, 1986

[54] TOTAL ORGANIC CARBON ANALYZER

[75] Inventor: Bernie B. Bernard, College Station, Tex.

[73] Assignee: O.I. Corporation, College Station, Tex.

[21] Appl. No.: 635,147

[22] Filed: Jul. 27, 1984

[51] Int. Cl.$^4$ .................................. G01N 33/00
[52] U.S. Cl. ....................... 436/145; 436/146; 422/78; 422/79; 422/80
[58] Field of Search ............. 436/145, 146; 422/79, 422/80, 78

[56] References Cited

U.S. PATENT DOCUMENTS

| | | | |
|---|---|---|---|
| 3,784,359 | 1/1974 | Parth | 422/79 |
| 3,864,088 | 2/1975 | Delin et al. | 422/80 |
| 4,066,402 | 1/1978 | Komiyama et al. | 436/145 |
| 4,401,763 | 8/1983 | Itoh | 436/145 |

OTHER PUBLICATIONS

Baldwin and McAtee, "Determination of Organic Carbon in Water with a Silver–Catalyzed Peroxydisulfate Wet Chemical Oxidation Method", 19 *Microchem. J.* 179 (1974).

Osburn and Werkman, "Determination of Carbon in Fermented Liquors", *Ind. and Eng. Chem.* 421 (1932).
Menzel and Vaccaro, "The Measurement of Dissolved Organic and Particulate Carbon in Seawater", 9 *Limnol. Oceanogra.* 138 (1964).
Goulden and Brooksbank, "Automated Determinations of Dissolved Organic Carbon in Lake Water", *Anal. Chem.* 1943 (1975).

*Primary Examiner*—Peter Chin
*Attorney, Agent, or Firm*—Richards, Harris, Medlock & Andrews

[57] ABSTRACT

An improved digestion chamber (10) is provided for use in a carbon analysis system. A catalyst (16), selected from the platinum metals group consisting of platinum, rhodium, palladium, osmium, iridium and ruthenium, provides an oxidizing surface for the sample being analyzed. The oxidant (26) is preferably persulfate, which may be stored in a generally stable solution until needed for sample oxidation. The catalyst (16) may be provided as a digestion chamber wire insert, such as a rod or as a plating on the chamber walls, enabling an increased variety of materials to be used for the vessel. In a preferred embodiment of the digestion chamber, polytetrafluoroethylene is used to reduce the background carbon which must be corrected in the analysis.

3 Claims, 4 Drawing Figures

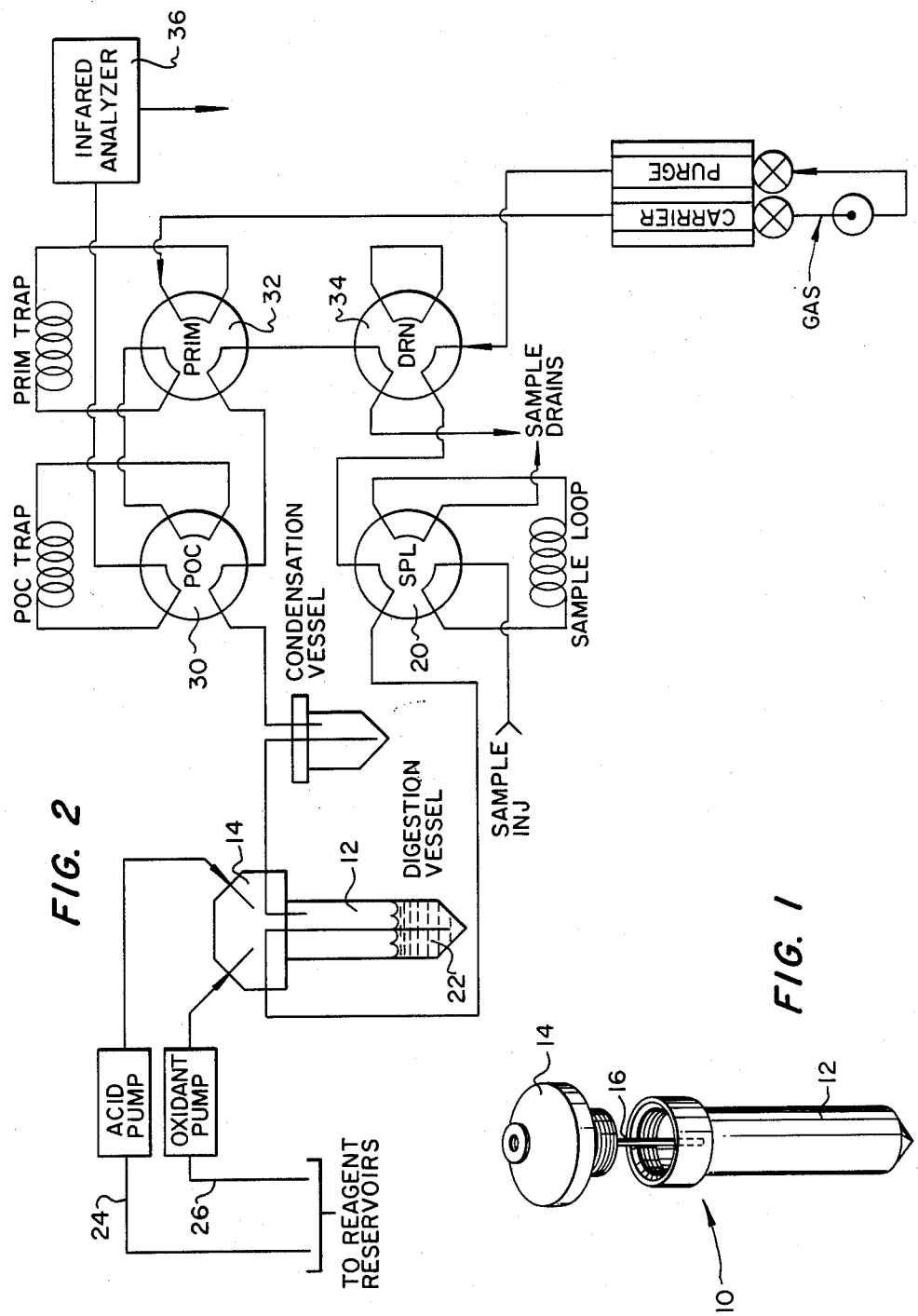

4,619,902

TOTAL ORGANIC CARBON ANALYZER

TECHNICAL FIELD

This invention relates to the analysis of total organic carbon in a material sample and, more particularly, to improving the efficiency and reaction time between an oxidant and organic carbon sought to be measured.

BACKGROUND ART

The measurement of organic carbon in a material sample provides information relevant to the hazardous nature of the material, if consumed, and possible contamination of the environment, if discharged. In a conventional process, acid is first used to generate carbon dioxide ($CO_2$) from inorganic carbon. This $CO_2$ is removed prior to oxidation of the residual organic carbon to $CO_2$. $CO_2$ from oxidation of organics is then measured.

A preferred oxidant for an aqueous solution including the remaining organic carbon compounds is potassium peroxydisulfate ("persulfate"), $K_2S_2O_8$, for generating $CO_2$. See, for example, Osburn and Werkman, "Determination of Carbon in Fermented Liquors," *Ind. and Eng. Chem.* 421 (1932); Menzel and Vaccaro, "The Measurement of Dissolved Organic and Particulate Carbon in Seawater," 9 *Limnol. Oceanogra.* 138 (1964). In a standard process for generating $CO_2$ for carbon analysis, persulfate is provided with the sample for oxidation in a glass ampule and the ampule is sealed by melting the ends of the glass ampule. The sealed ampule is heated to promote the oxidation of organic carbon in the sample and the ampule is thereafter opened for $CO_2$ measurement.

A principal disadvantage of the wet oxidation process is that a long reaction time is needed for an efficient oxidation with persulfate. A silver catalyst in the form of $AgNO_3$ has been used to improve the reaction speed and to improve oxidation efficiencies. See, for example, Goulden and Brooksbank, "Automated, Determinations of Dissolved Organic Carbon in Lake Water," 47 *Anal. Chem.*, 1943 (1975); Baldwin and McAtee, "Determination of Organic Carbon in Water with a Silver-Catalyzed Peroxydisulfate Wet Chemical Oxidation Method," 19 *Microchem. J.* 179 (1974). However, the $AgNO_3$ is consumed in the reaction process and also greatly increases the rate of auto-degradation of persulfate. Further, the resulting solution contains silver ions and must be treated for environmental discharge purposes and/or for silver reclamation.

The prior art processes generally require attended and/or batch operation. If $AgNO_3$ is not used, the reaction time is too great for any continuous operation. If $AgNO_3$ is used, the supply must be replenished, the reaction waste treated and the $AgNO_3$ freshly mixed with persulfate.

In many of the prior art analytical techniques the reaction occurs in sealed ampules of glass. It has been found that glass, while inert, contributes some carbon during $CO_2$ generation, as indicated by "carbon blank", or test runs with zero carbon. The "carbon blank" values of glass are in the range of 1 microgram of carbon ("$\mu g$ C") per ampule and these values limit the sensitivity of the analysis to about 2 $\mu g$ C per ampule.

Due to the nature of the solutions introduced into the reaction vessel, including acids and oxidants, material selections for the vessel are limited. A suitable material should not increase the carbon blank value, should not react with the analysis solutions and should be readily flushed between samples.

The above disadvantages of the prior art are overcome with the present invention wherein improvements in design and operation of a digestion vessel are provided for sample oxidation.

SUMMARY OF THE INVENTION

An improved digestion vessel assembly is provided for use in a system for determining the total organic carbon present in a sample. The sample is introduced within a digestion vessel assembly which is effective to contain the solutions used in the analysis. A catalyst selected from the platinum metals group consisting of platinum, rhodium, palladium, osmium, iridium and ruthenium is provided in the vessel to provide a surface for reacting an oxidant with the carbon in the sample.

The oxidant may be separately maintained and introduced into the digestion vessel as needed to generate carbon dioxide from a sample using a catalytic surface.

In one embodiment of the present invention, the catalyst is provided as a digestion vessel plating to enable the use of common metals for the vessel.

In another embodiment of the present invention, the digestion vessel is formed of polytetrafluoroethylene for a reduced carbon blank.

One feature of the present invention is the capability for unattended and process monitoring operations.

Another feature is improved sensitivity for low carbon concentrations.

One other feature is catalyst stability over the operating parameters and in the presence of process chemicals.

These and other features and advantages of the present invention will become apparent from the following detailed description, wherein reference is made to the figures in the accompanying drawings.

BRIEF DESCRIPTION OF THE DRAWINGS

FIG. 1 is a pictorial illustration of one embodiment of the present invention;

FIG. 2 is a simplified schematic of a carbon analysis system;

DETAILED DESCRIPTION

Figure 3:
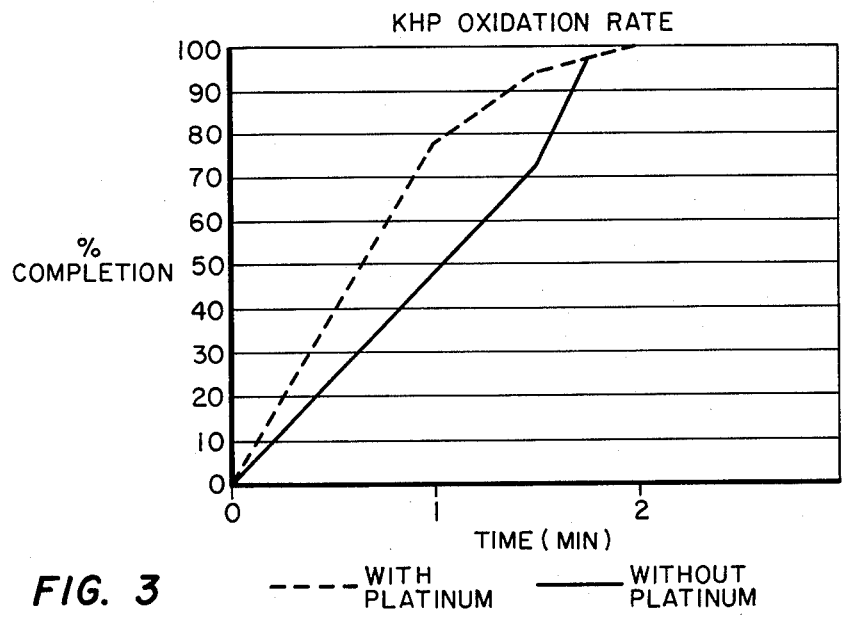
FIG. 3 is a graphic illustration including potassium hydrogen phthalate as the working sample.

As hereinabove indicated, some of the problems presently associated with obtaining a carbon analysis include:

1. lack of a permanent catalyst;
2. carbon contamination from system components;
3. time requirements for complete oxidation of the sample; and
4. efficient utilization of the oxidant. The vessel depicted in FIG. 1 solves the above problems while producing carbon dioxide ($CO_2$) from the sample under investigation.

As shown in FIG. 1, digestion chamber assembly 10 is provided. Digestion vessel 12 is provided with top fitting 14 adapted for material flow to and from adjacent system components. As shown in FIG. 1, catalyst 16 is provided for improving the speed of reaction and the efficiency of oxidant utilization.

Digestion vessel 12 must accommodate the sample and the sample processing fluids and must be compatible with such fluids. Typical reagents used to digest the carbon-containing samples for processing include acids for dissolving the sample and/or reacting with inorganic carbon compounds and an oxidant for generating $CO_2$ from carbon in the sample. Many inert materials, such as glass, fulfill these requirements.

In one embodiment of the present invention, catalyst 16 is provided in the form of a wire, or other form of insert, and vessel 12 and top fitting 14 may be a polytetrafluoroethylene, such as Teflon. Catalyst 16 is selected from the platinum metal group of platinum, iridium, osmium, palladium, rhodium and ruthenium. Platinum is a preferred material where catalyst 16 is provided as a wire. As hereinafter described, a catalyst such as platinum improves the efficiency of the oxidation process for sample digestion. An inert vessel material such as polytetrafluoroethylene enables the more efficient oxidation to be used in improving the system sensitivity by reducing the "carbon blank" which is generally required to correct for carbon contamination in the system.

Conventional inert materials, such as glasses, typically release carbon in the amount of about 1 microgram of carbon for a standard size ampule of sample being digested. Sample measurements indicating less than about 2 micrograms of carbon per ampule are, thus, not generally determinable. However, in accordance with one embodiment of the present invention, polytetrafluoroethylene ("PTFE") is used to reduce this "blank" to the equivalent of 0.25 micrograms of carbon per ampule. Thus, the sensitivity of measurement is greatly increased by the selection of the polytetrafluoroethylene material.

The design of a digestion vessel 12 with polytetrafluoroethylene must also consider the permeable nature of the material. If the vessel is made too thin, the generated $CO_2$ may diffuse through the wall structure and escape. If the vessel thickness is made too great, the heating time for the liquid within the vessel becomes too great due to the insulating property of PTFE. There exists a range of suitable thicknesses and a thickness of 0.02875 inches has been found to be thin enough to obtain the desired heat transfer and thick enough for measurement accuracy. In particular, the fluid sample within the vessel can obtain an operating temperature in the preferred range of 90°–100° C. in twenty seconds when vessel 12 is placed within a heating chamber, a time equivalent to heating the fluid volume alone without insulating barriers. In addition, the results have been found to be repeatable within 0.5% and recoverable within 0.5%, indicating that gas diffusion through the porous vessel is insignificant.

In yet another embodiment, catalyst 16 may be provided in the form of an interior plating for digestion vessel 12 in order to greatly increase the contact surface area between the material being oxidized and the catalyst for increased reaction speed. Catalyst materials selected from the platinum group are generally inert and may be used to form an integral plating, enabling vessel materials to be used which would otherwise be unsuitable. In particular, metallic vessels of stainless steel, aluminum or brass may be plated and used. These plated vessels might be expected to even further reduce the "carbon blank" while providing improved heat transfer for reaching oxidation temperature.

Referring now to FIG. 2, there is shown, in schematic form, a carbon analyzer system using the digestion chamber assembly depicted in FIG. 1. The carbon analyzer includes sample valve 20 for introducing a sample within digestion vessel 22. An acid pump introduces acid through line 24 for dissolving the sample and generating $CO_2$ from inorganic carbon. While persulfate is the preferred oxidant other conventional oxidants such as perchlorate permanganate, dichromate, ozone, peroxide, sulphuric acid or nitric acid, may be used based on the specific application, need for solution stability, availability of oxidant, etc. An oxidant pump is also provided for injecting an oxidant through line 26 to generate $CO_2$ from organic carbon in the system. POC (purgeable organic carbon) valve 30 and PRIM (primary) valve 32 act in sequence to trap the evolved $CO_2$ as a purge gas is introduced to move the $CO_2$ evolved from fluid 22 within digestion vessel 12 into absorption traps.

When $CO_2$ evolution and absorption is complete, a carrier gas desorbs the $CO_2$ from the absorption traps for movement through infrared analyzer 36, which measures the carbon dioxide present in the gas stream.

Drain valve 34 may now be operated to enable purge gas to carry the spent sample out of digestion vessel 12 and out of the sample drains for disposal. Valves 20, 30, 32 and 34 are six-port valves where adjacent ports may be connected to direct material flow through the valve. As shown in FIG. 2, the port pairs are shown connected for moving evolved $CO_2$ for infrared analysis and for sample drain.

The system shown in FIGS. 1 and 2, and discussed above, was used to analyze the carbon content of ultrapure water. A total organic carbon concentration down to about 30 ppb carbon was repeatably obtained, a concentration heretofore believed to be too low to measure with any accuracy.

As shown in FIG. 2, the operational sequence can be automated to enable a continuous and/or an automatic system of analysis using a catalyst selected from the platinum group. The selected catalyst remains unchanged during the $CO_2$ generation, does not require replenishment during operation and does not degrade the oxidant.

Silver nitrate ($AgNO_3$) heretofore used to increase the oxidation efficiency does not appear suitable for a continuous, or process monitoring, operation. A silver wire or plating would be corroded by the chemicals used in the process and $AgNO_3$ as a catalyst is consumed during the reaction, such that the sample waste contains waste silver and has to be further processed for either silver reclamation or sample discharge. If automation were to be attempted, it would appear that a separate injection system would be required for the $AgNO_3$ since pre-mixing $AgNO_3$ with persulfate reduces the storage life of the mixture to only a few hours.

As noted above, persulfate has long been preferred as an oxidant, but persulfate tends to auto-degrade in solution, a process which is enhanced by $AgNO_3$. Thus, a water solution of persulfate at room temperature will subsist for months if stored in its own container. If $AgNO_3$ is now added to the oxidant container, the auto-degradation time is reduced to a few hours. Thus, providing an automatic or unattended system to use $AgNO_3$ requires a substantial increase in system complexity over the system utilizing a catalyst selected from the platinum metal group.

Persulfate tends to auto-degrade and this degradation increases with temperature. Higher temperatures enhance the auto-degradation over the oxidation reaction. The time for degradation can act to reduce the amount of persulfate in a sample below the amount needed to effect complete oxidation of the sample. The platinum catalyst, however, tends to enhance the oxidation reaction over the auto-degradation mechanism. This enhancement enables less persulfate to be added to achieve a given amount of oxidation in a set time and enables a higher temperature to be used for the oxidation to improve the speed of reaction.

Figure 4:
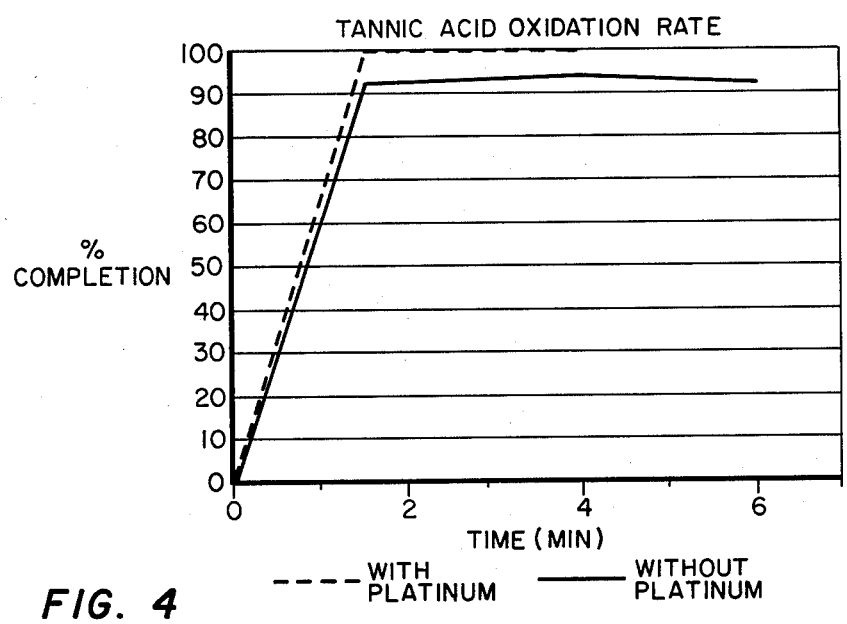
FIG. 4 is a graphic illustration including tannic acid as the working sample.

FIGS. 3 and 4 tend to demonstrate the above improved operational effects of a platinum catalyst. For all of the reactions depicted in FIGS. 3 and 4, the quantity of oxidant was 600 microliters of a solution formed by mixing 50 grams of persulfate in a liter of water. It should be noted that a relatively high concentration of persulfate is used, where a saturation mixture at room temperature is about 60 grams of persulfate in a liter of water. An oxidation temperature in the range of 90°–100° C., and preferably 95° C., was used. FIG. 3 illustrates the reaction kinetics with potassium hydrogen phthalate and shows that the reaction with platinum generally proceeds at a faster rate than the reaction without the platinum. In FIG. 4, there is shown the kinetics of oxidizing tannic acid. FIG. 4 illustrates that the oxidation reaction goes to completion when platinum is included as a catalyst, but the same amount of persulfate does not enable the reaction to be completed where reaction occurs without a platinum catalyst. This is believed to result from the persulfate auto-degrading before completely oxidizing the tannic acid.

FIGS. 3 and 4 were obtained from reaction kinetics where a platinum wire insert was used. The wire insert may be in the form of a rod, may be coiled, may be a mesh, etc. It is believed that the use of a plated vessel would enable even more dramatic results to be obtained to illustrate substantially complete oxidation within an extremely short period of time and with reduced use of persulfate.

It is therefore apparent that the present invention is one well adapted to attain all of the objects and advantages hereinabove set forth together with other advantages which will become obvious and inherent from a description of the system and process. It will be understood that certain combinations and subcombinations are of utility and may be obtained without reference to other features and subcombinations. This is contemplated by and is within the scope of the present invention.

As many possible embodiments may be made of this invention without departing from the spirit or scope thereof, it is to be understood that all matters herein set forth in the accompanying drawings are to be interpreted as illustrative and not in any limiting sense.

I claim:

1. A process for analyzing the carbon content of a carbon-containing sample by reacting said sample with an oxidizing agent in a wet oxidation process to generate carbon dioxide in a digestion chamber, comprising the steps of:
   introducing said oxidizing agent within said digestion chamber;
   introducing said sample within said digestion chamber;
   contacting said sample with said oxidizing agent on a catalytic surface formed from a member of the platinum materials group consisting of platinum, rhodium, paladium, osmium, iridium and ruthenium;
   heating said sample and said oxidizing agent contacting said catalytic surface to a temperature in a range effective to generate carbon dioxide in a liquid phase oxidation reaction;
   withdrawing said carbon dioxide from said digestion chamber; and
   analyzing said carbon dioxide withdrawn from said digestion chamber.

2. The process according to claim 1, wherein said oxidizing agent is selected from a group consisting of persulfate, perchlorate, permanganate, dichromate, ozone, peroxide, sulphuric acid and nitric acid.

3. The process according to claim 1, wherein said temperature range is 90 degrees to 100 degrees Centigrade.

* * * * *